United States Patent
Girotra et al.

(10) Patent No.: US 11,633,588 B2
(45) Date of Patent: Apr. 25, 2023

(54) EARSET ASSEMBLY FOR PROVIDING IONTOPHORESIS INCLUDING VALVE

(71) Applicant: TUSKER MEDICAL, INC., Menlo Park, CA (US)

(72) Inventors: Rohit Girotra, San Francisco, CA (US); Eric Goldfarb, Belmont, CA (US); Andrew Lantz, Redwood City, CA (US); Elmer Yee, Dublin, CA (US)

(73) Assignee: TUSKER MEDICAL, INC., Menlo Park, CA (US)

( * ) Notice: Subject to any disclaimer, the term of this patent is extended or adjusted under 35 U.S.C. 154(b) by 369 days.

(21) Appl. No.: 16/961,428

(22) PCT Filed: Jan. 15, 2019

(86) PCT No.: PCT/US2019/013664
§ 371 (c)(1),
(2) Date: Jul. 10, 2020

(87) PCT Pub. No.: WO2019/143617
PCT Pub. Date: Jul. 25, 2019

(65) Prior Publication Data
US 2020/0353238 A1 Nov. 12, 2020

Related U.S. Application Data

(60) Provisional application No. 62/617,945, filed on Jan. 16, 2018.

(51) Int. Cl.
*A61F 11/08* (2006.01)
*A61N 1/04* (2006.01)
(Continued)

(52) U.S. Cl.
CPC ............ *A61N 1/0448* (2013.01); *A61F 11/08* (2013.01); *A61M 39/24* (2013.01); *A61N 1/325* (2013.01);
(Continued)

(58) Field of Classification Search
CPC . A61F 11/08; A61F 11/085; A61M 2039/242; A61M 19/00; A61N 1/0448
See application file for complete search history.

(56) References Cited

U.S. PATENT DOCUMENTS

| 4,166,457 A | 9/1979 | Jacobsen et al. |
| 8,840,602 B2 * | 9/2014 | Morriss ................ A61K 9/0046 604/501 |

(Continued)

FOREIGN PATENT DOCUMENTS

AU 2013209354 B2 7/2015

OTHER PUBLICATIONS

Patent Cooperation Treaty, International Search Report and Written Opinion for International Application No. PCT/US2019/013664, dated Jan. 4, 2019; 11 pages.

*Primary Examiner* — Deanna K Hall
(74) *Attorney, Agent, or Firm* — Dickinson Wright, PLLC

(57) ABSTRACT

Systems, apparatus, and methods are described for delivering a therapeutic substance, such as an anesthetic, to a tympanic membrane of a subject. Such systems can include an earset with a valve configured to control flow of a fluid, such as air, into and out of a reservoir. In some embodiments, systems, apparatus, and methods described herein can include additional valves and features for relieving negative pressure within the reservoir.

26 Claims, 14 Drawing Sheets

(51) Int. Cl.
*A61M 39/24* (2006.01)
*A61N 1/32* (2006.01)
*A61M 19/00* (2006.01)

(52) U.S. Cl.
CPC ............ *A61F 11/085* (2022.01); *A61M 19/00* (2013.01); *A61M 2039/242* (2013.01)

(56) References Cited

U.S. PATENT DOCUMENTS

2008/0262510 A1* 10/2008 Clifford ................. A61N 1/306
604/501
2016/0361204 A1 12/2016 Girotra et al.

* cited by examiner

EARSET ASSEMBLY FOR PROVIDING IONTOPHORESIS INCLUDING VALVE

CROSS-REFERENCE TO RELATED APPLICATIONS

This application is a U.S. National Phase Entry of PCT application Serial No. PCT/US2019/013664 filed Jan. 15, 2019 and titled "Earset Assembly for Providing Iontophoresis Including Valve." The PCT application claims priority to and the benefit of U.S. Provisional Patent Application No. 62/617,945, filed Jan. 16, 2018, entitled "Earset Assembly for Providing Iontophoresis Including Valve." The PCT application and the provisional application are both incorporated herein by reference in their entirety.

TECHNICAL FIELD

The present disclosure relates generally to systems, apparatuses, and methods for delivering a substance to an ear of a subject using iontophoresis. More specifically, the present disclosure relates to an earset assembly having a valve design for use in iontophoretic delivery of a therapeutic substance, such as an anesthetic, to a tympanic membrane of a subject.

BACKGROUND

Otitis media is an inflammation of the middle ear and is particularly common in human children due to their anatomy and immune function. If severe or untreated, otitis media may result in rupture of an individual's tympanic membrane, hearing loss, or intracranial complications.

Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. To reduce those risks, a local anesthesia delivery method can be used. Some pressure equalization tube delivery systems and methods, for example, provide an anesthetic through iontophoresis to an area around and including the tympanic membrane.

Iontophoresis involves the application of a low-level electric current to a charged drug solution. The electric current repels similarly charged ions of the drug within the solution and transports them across the skin or other membrane. In ear procedures, iontophoresis can be used to anesthetize the tympanic membrane before placing a tympanostomy tube across it. In these procedures, a drug solution is placed in an ear canal and current is applied to the solution via an electrode, thus transporting an anesthetic within the drug solution across the tympanic membrane.

Existing and previously described iontophoresis devices and systems have certain shortcomings. For example, some devices do not seal the drug solution in an ear canal, which would require a patient to recline and tilt his/her head during an iontophoresis procedure. Further, prior devices that seal the drug solution in the ear canal, such as devices including an earplug, may not conform adequately to the curved anatomy of the ear canal and thus fail to form a good seal in the ear canal of at least some patients. When a seal is not formed, fluid from within the ear canal may leak out, leading to the formation of bubbles that can interfere with contact between an iontophoretic electrode and the solution. Therefore, it is desirable to have an iontophoresis system that accounts for these and other shortcomings.

SUMMARY

Systems, apparatus, and methods are described for delivering a substance to an ear of a subject, and in particular the tympanic membrane of the subject. The therapeutic substance may be an anesthetic, such as lidocaine, which may be used to anesthetize the tympanic membrane in preparation for piercing the membrane, e.g. for a myringotomy or tympanostomy, or tympanocentesis.

According to some embodiments, an apparatus for delivering an anesthetic to an ear of a subject includes a body defining a channel, a reservoir in fluid communication with the channel, and a vent path in fluid communication with the reservoir. An electrode can be disposed within the channel and be configured to apply a current to a drug solution (i.e., an iontophoresis solution having a charged drug) within the channel and/or reservoir. The vent path can allow air and/or fluid to escape the reservoir when the reservoir is filled with the drug solution. A one-way valve can be positioned in the vent path to prevent and/or limit air from re-entering the reservoir via the vent path, thereby reducing leakage of drug solution out of the reservoir and a risk of disruption of the iontophoresis procedure. In some embodiments, the one-way valve can be an umbrella valve. In some embodiments, the one-way valve can be designed to relieve negative pressure within the channel and/or reservoir of the apparatus. For example, the one-way valve can be designed to fail and allow air to re-enter the reservoir when a negative gauge pressure of 1 kPa is reached.

In some embodiments, a fluid source can be used to supply the drug solution to the channel and/or reservoir. The fluid source can be, for example, a syringe. The apparatus is in fluid communication with fluid source via one or more connectors and/or conduits. The connectors and/or conduits can include an adapter that prevents backflow of a fluid from the apparatus to the fluid source, thereby reducing a risk of negative pressure buildup within the apparatus. In some embodiments, the adapter may include a one-way valve designed to allow forward flow of a fluid from the fluid source to the channel and/or reservoir of the apparatus but prevent backward flow of a fluid from the apparatus back toward the fluid source.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 2A provides a perspective view of the earset, and FIG. 2B provides a cross-sectional view of the earset along line 2B-2B of FIG. 2A.

FIG. 7A depicts the one-way valve in a resting configuration in which air and/or fluid from within the earset does not flow in or out of the earset, and FIG. 7B depicts the one-way valve in a positive-pressure configuration in which air and/or fluid from within the earset can flow out via the vent path.

FIG. 8A depicts the valve in a resting configuration in which air and/or fluid from outside of the earset cannot enter the earset, and FIG. 8B depicts the valve in a negative-pressure configuration in which air and/or fluid from outside can flow into the earset via the vent path.

FIG. 11A depicts the one-way valve component in a first configuration in which fluid flows out of a fluid source, and FIG. 11B depicts the one-way valve component in a second configuration in which fluid cannot flow toward the fluid source.

DETAILED DESCRIPTION

Systems, apparatus, and methods are described herein for an iontophoresis system. In some embodiments, the iontophoresis system can be used to anesthetize an ear of a subject before deployment of a tympanostomy tube in the tympanic membrane of the subject.

A tympanostomy tube or pressure equalization tube can be deployed in a tympanic membrane of a patient to treat, for example, otitis media. In some embodiments, a delivery instrument can be used to insert a tympanostomy tube in the tympanic membrane. Examples of tympanostomy tube delivery systems are disclosed in U.S. Pat. No. 8,052,693, titled "System and Method for the Simultaneous Automated Bilateral Delivery of Pressure Equalization Tubes," issued Nov. 8, 2011; U.S. Pat. No. 8,864,774, titled "Tympanic Membrane Pressure Equalization Tube Delivery System," issued Oct. 21, 2014; U.S. Pat. No. 9,320,652, titled "Features to Improve and Sense Tympanic Membrane Apposition by Tympanostomy Tube Delivery Instrument," issued Apr. 26, 2016; U.S. Pat. No. 9,681,891, titled "Tympanostomy Tube Delivery Device with Cutting Dilator," issued Jun. 20, 2017; U.S. Patent Application Publication No. 2016/0038342, titled "Tympanostomy Tube Delivery Device with Rotatable Flexible Shaft," published Feb. 11, 2016; and U.S. Pat. No. 9,833,360, titled "Tympanostomy Tube Delivery Device with Replaceable Shaft Portion," issued Dec. 5, 2017. The disclosures of each of these references are incorporated herein by reference. In some embodiments, a tympanostomy tube can be inserted into the tympanic membrane manually, e.g., by creating a myringotomy incision with a cutting tool and inserting the tympanostomy tube into the incision using forceps, etc.

In some embodiments, an iontophoresis system can include an earset with a flexible sealing element or earplug that is configured to form a fluid tight seal against a surface of an ear of a subject. The earset can define a volume within the ear into which an iontophoresis fluid can be delivered. The iontophoresis system can include an electrode that can be activated to supply a current to the iontophoresis fluid to drive ions of a drug (e.g., anesthetic) into the tympanic membrane. Examples of iontophoresis systems are disclosed in U.S. Pat. No. 8,452,392, titled "Systems and Methods for Anesthetizing Ear Tissue," issued May 27, 2013; U.S. Pat. No. 8,840,602, titled "Systems and Methods for Anesthetizing Ear Tissue," issued Sep. 23, 2014; and U.S. Patent Application Publication No. 2017/0014272, titled "Earplug Assembly for Iontophoresis System," published Jan. 19, 2017. The disclosures of each of these references are incorporated herein by reference.

Figure 1:
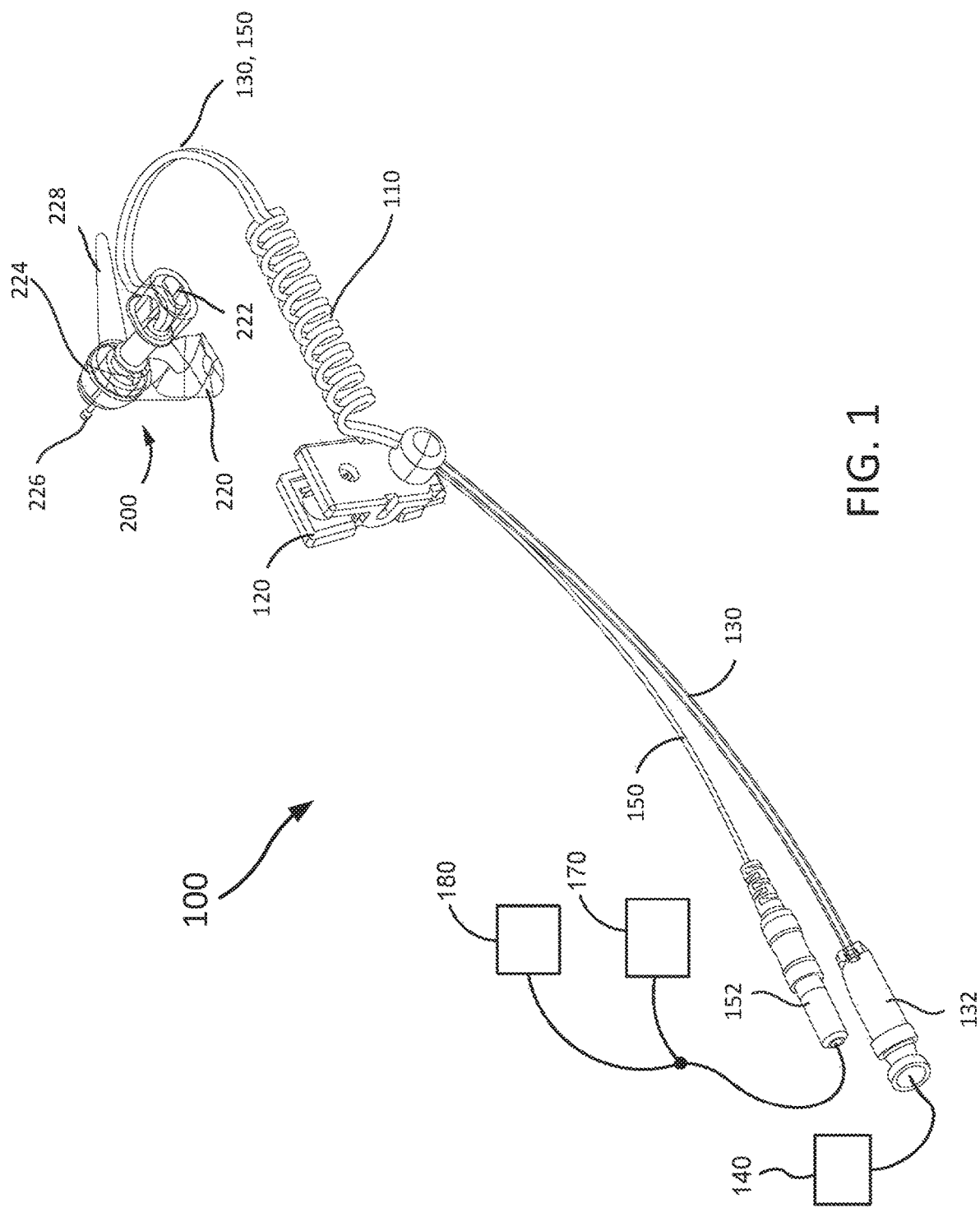
FIG. 1 illustrates an example of an iontophoresis system including an earset, in accordance with some embodiments.

FIG. 1 illustrates an example of an iontophoresis system 100, including an earset 200. Earset 200 is in communication with a fluid source 140 (e.g., a syringe) via a connector 132 and a conduit 130. In an embodiment, conduit 130 can be in the form of flexible tubing. Earset 200 is also in communication with a control unit 170 and a ground pad 180 via a connector 152 and a cable 150. Conduit 130 and cable 150 are coupled together along a shared length extending between a clip 120 and earset 200. A portion 110 of the shared length of conduit 130 and cable 150 can be coiled, and can expanded and/or contracted to adjust the distance between clip 120 and earset 200. Clip 120 is operable to selectively secure the combination of conduit 130 and cable 150 to clothing and/or to any other suitable structure such that iontophoresis system 100 can be secured to a subject during an iontophoresis procedure.

Figure 2A:
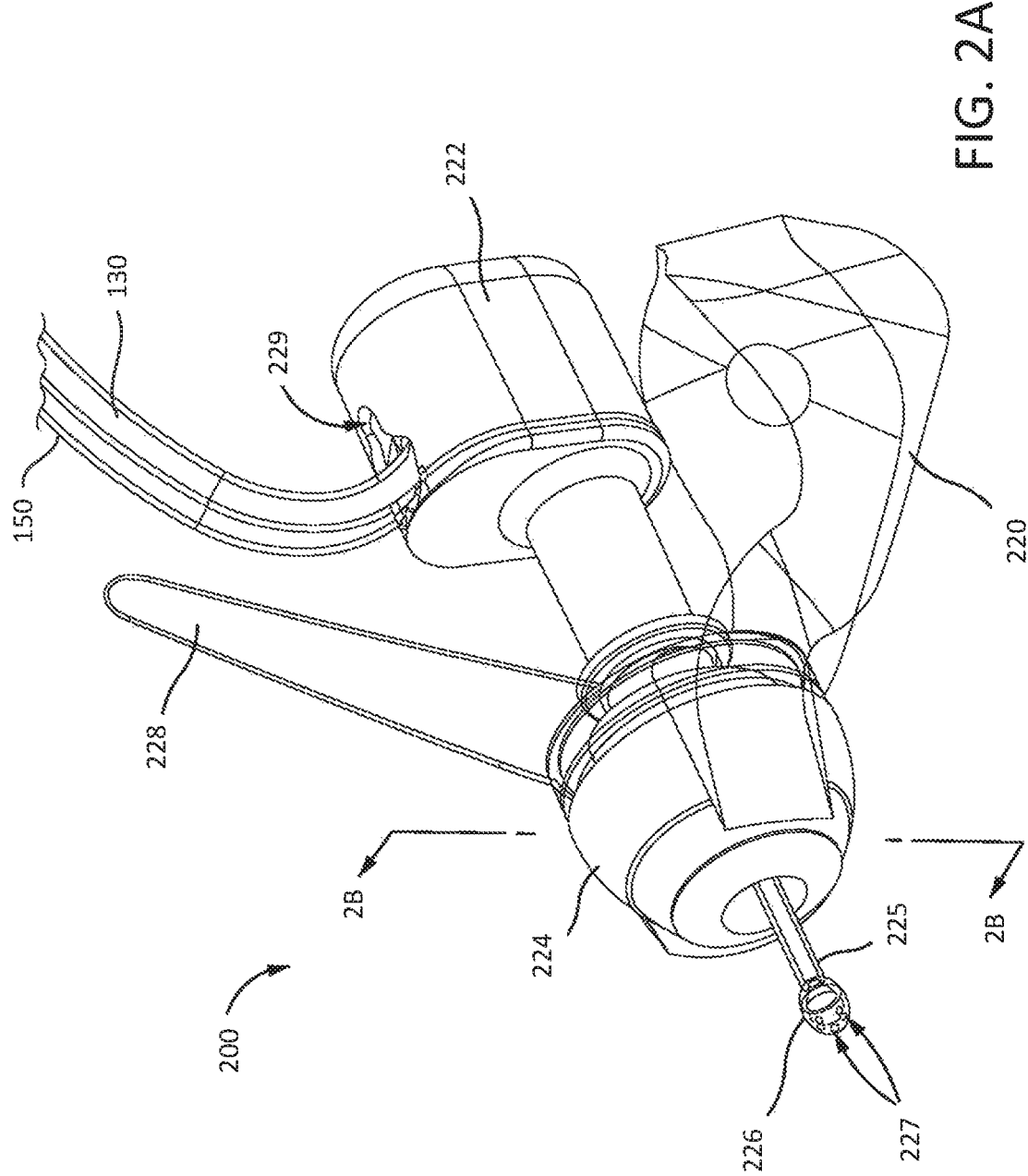
FIGS. 2A and 2B are illustrations of an example earset, in accordance with some embodiments.
Figure 2B:
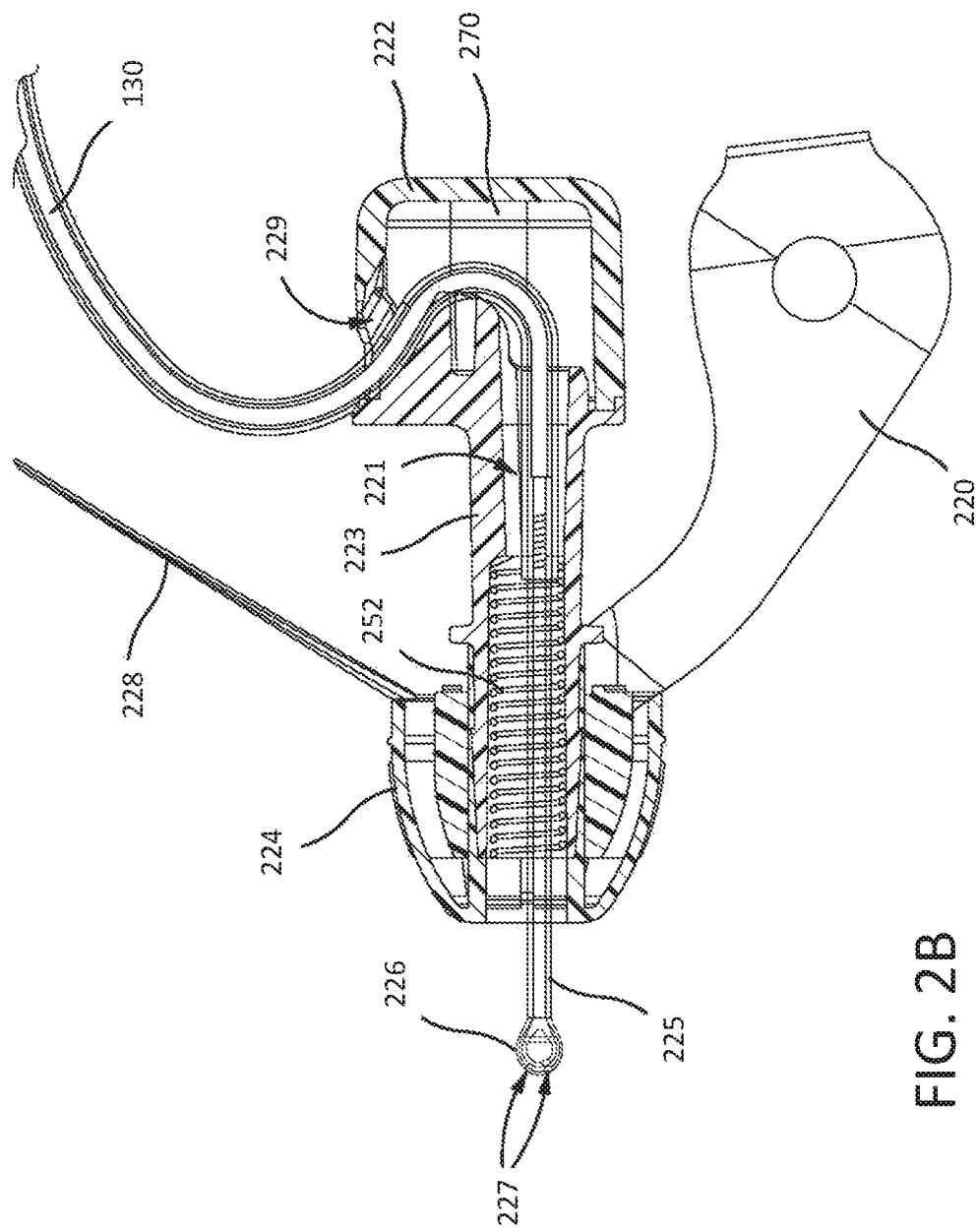

FIGS. 2A and 2B provide detailed views of earset 200. FIG. 2A provides a perspective view of earset 200, and FIG. 2B provides a cross-sectional view of earset 200 taken along the line 2B-2B in FIG. 2A. Earset 200 can be inserted into an ear and remain within the ear without requiring additional attachment components (e.g., a headframe). In some embodiments, earset 200 can have a biocompatible pressure sensitive adhesive that can assist in holding earset 200 in place within the ear. Earset 200 includes an insertion element such as a gripping feature 222 that can be gripped by a user and serve as a handle during insertion of earset 200 into the ear. Earset 200 also includes a retrieval element such as a pull-tab 228 that can be gripped and pulled to assist in removing earset 200 from the ear. In some embodiments, other kinds of insertion and/or retrieval elements can be incorporated into earset 200. While one earset 200 is shown, it should be understood that iontophoresis system 100 can have two earsets 200 that can be used in both ears of a subject to provide simultaneous and/or sequential delivery of a therapeutic substance via iontophoresis.

Earset 200 includes a flexible sealing element or earplug 224 and a distally projecting nozzle 226. Sealing element 224 is configured to provide a fluid tight seal against a surface of the ear canal when earset 200 is inserted in the ear. In some embodiments, a pressure sensitive adhesive is applied to the outer surface of sealing element 224 to promote a fluid tight seal against the ear canal. Nozzle 226 is positioned to project into the ear canal when earset 200 is inserted in the ear, such that nozzle 226 is spaced lateral to a tympanic membrane, such that tympanic membrane TM shown in FIGS. 3A-3C. Nozzle 226 has a plurality of spray apertures 227 and is secured to the distal end of post 225. Post 225 defines a lumen providing a path for communication of fluid from conduit 130 to spray apertures 227. In an embodiment, post 225 can be a semi-rigid post, which can bend and thereby adjust the direction of spray of spray apertures 227. Spray apertures 227 are thus in fluid communication with fluid source 140 via post 225 and conduit 130. Sealing element 224 is secured to a rigid frame 223. Sealing element 224 and frame 223 together define a working channel 221.

Gripping feature 222 is fixedly secured to rigid frame 223. Gripping feature 222 and frame 223 cooperate to define a reservoir 270. Reservoir 270 is in fluid communication with working channel 221. Reservoir 270 extends laterally relative to a longitudinal axis defined by post 225. Thus, reservoir 270 and working channel 221 together form an L-shaped cavity. The L-shaped cavity operates to maintain fluid contact with an iontophoresis electrode 252 even when the ear canal experiences volumetric changes throughout an iontophoresis procedure. Frame 223 also defines at least one vent path 229, which is also in fluid communication with reservoir 270. Vent path 229 is configured to allow a fluid (e.g., air and/or liquid) to escape reservoir 270 and working channel 221 when reservoir 270 and working channel 221 fills with iontophoresis solution, as will be described in greater detail below. Vent path 229 can be formed as a circular opening. In an embodiment, vent path 229 can be a circular opening having a diameter of approximately 0.025 inches. Alternatively, vent path 229 can have a different size and/or configuration. For example, vent path 229 can include separately formed openings that have the same or different shapes and/or sizes.

As depicted in FIG. 2B, an iontophoresis electrode 252 extends along a length of working channel 221. In the embodiment shown, iontophoresis electrode 252 is shaped as a coil, and is positioned along an inner surface of rigid frame 223. In other embodiments, iontophoresis electrode 252 can have different configurations. For example, iontophoresis electrode 252 can include one or more straight wires that extend along a length of working channel 221. In some embodiments, iontophoresis electrode 252 can be positioned adjacent to a wall or surface of rigid frame 223. In other embodiments, iontophoresis electrode 252 can be positioned within working channel 221 spaced from rigid frame 223.

Iontophoresis electrode 252 is coupled with control unit 170 via cable 150 and can be activated by control unit 170. Control unit 170 can activate iontophoresis electrode 252 to provide an electric current to the iontophoresis solution such that charged ions within the solution are delivered into the tympanic membrane TM. In the case of anesthetizing the tympanic membrane TM, the iontophoresis solution can include a charged anesthetic drug (e.g., lidocaine) for anesthetizing the tympanic membrane TM. Fluid source 140 can supply the iontophoresis solution including a therapeutic substance (e.g., an anesthetic such as lidocaine) to the earset 200. And control unit 170 can activate the iontophoresis electrode 252 to drive ions of the therapeutic substance within the iontophoresis solution into tissue including the tympanic membrane TM.

Reservoir 270 increases the volume of space within earset 200 that contains iontophoresis fluid. In some embodiments, reservoir 270 can have a volume that is at least twice the volume of working channel 221. By increasing the volume of iontophoresis fluid within earset 200, reservoir 270 reduces the risk that electrode 252 may become exposed to air, e.g., in the case of an air bubble that forms within the iontophoresis fluid within the earset 200. In instances where the entire electrode 252 or a substantial portion of the electrode 252 is exposed to air, the electrode 252 may not supply sufficient current to the iontophoresis fluid to deliver the therapeutic substance to the tympanic membrane TM. Reservoir 270 reduces this risk, as explained in further detail with reference to FIGS. 3C and 4.

Vent path 229 is positioned adjacent to reservoir 270 such that fluid (e.g., air and/or fluid) can exit out of the reservoir 270 via the vent path 229. As depicted in FIG. 3B, vent path 229 can be positioned at a lateral end of reservoir 270 such that any open space (e.g., air bubbles) that results from fluid exiting reservoir 270 remains within reservoir 270 adjacent to its lateral end and thereby spaced from the iontophoresis electrode 252. Vent path 229 can be formed integrally with an opening for receiving conduit 130. Alternatively, vent path 229 can be a separate opening formed in the earset 200, e.g., an opening formed in gripping feature 222 spaced away from the point at which conduit 130 enters gripping feature 222.

Figure 3A:
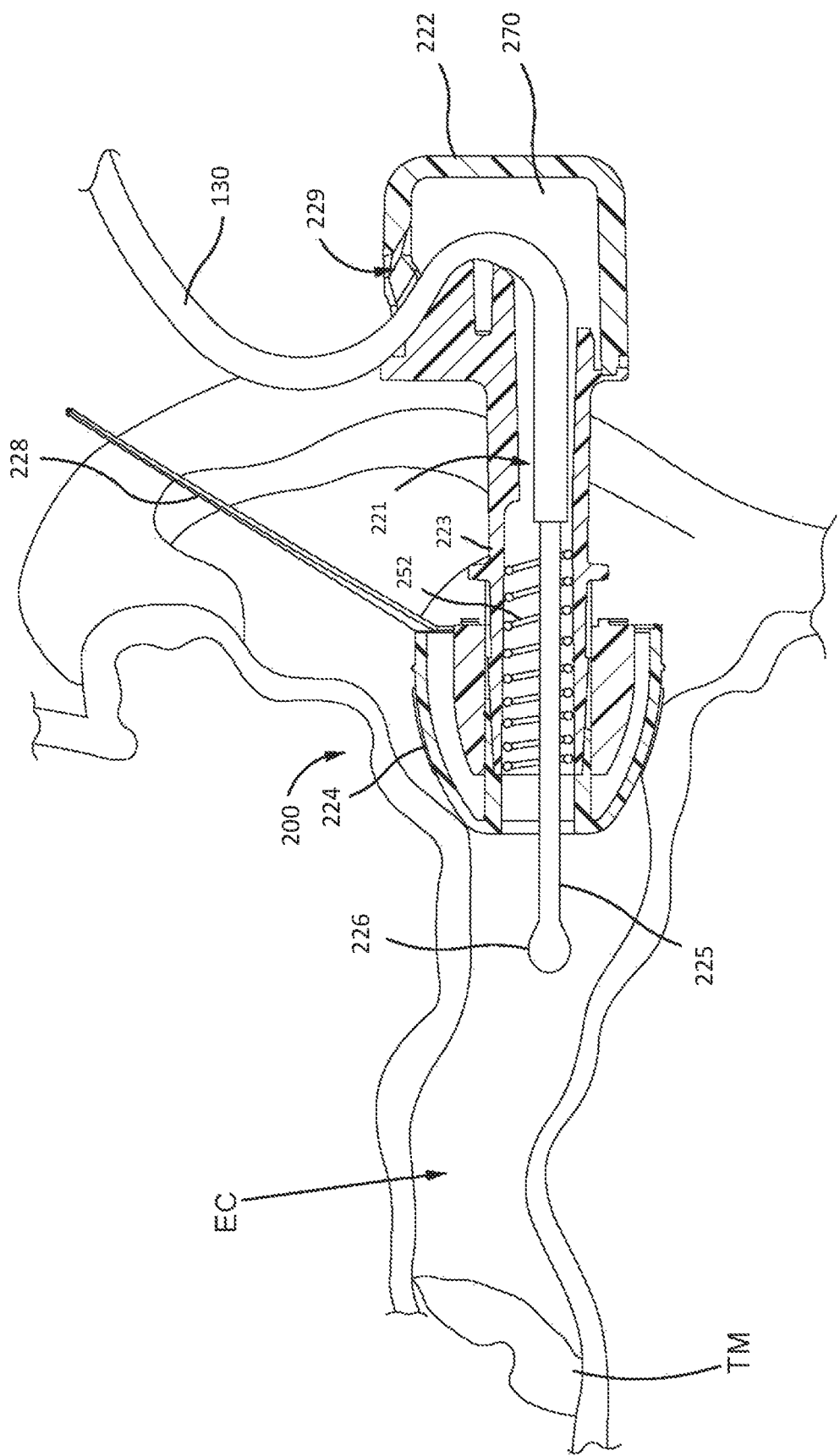
FIG. 3A depicts a cross-sectional view of the earset of FIGS. 2A and 2B, with the earset positioned adjacent to an ear of a subject at a horizontal orientation, in accordance with some embodiments.
Figure 3B:
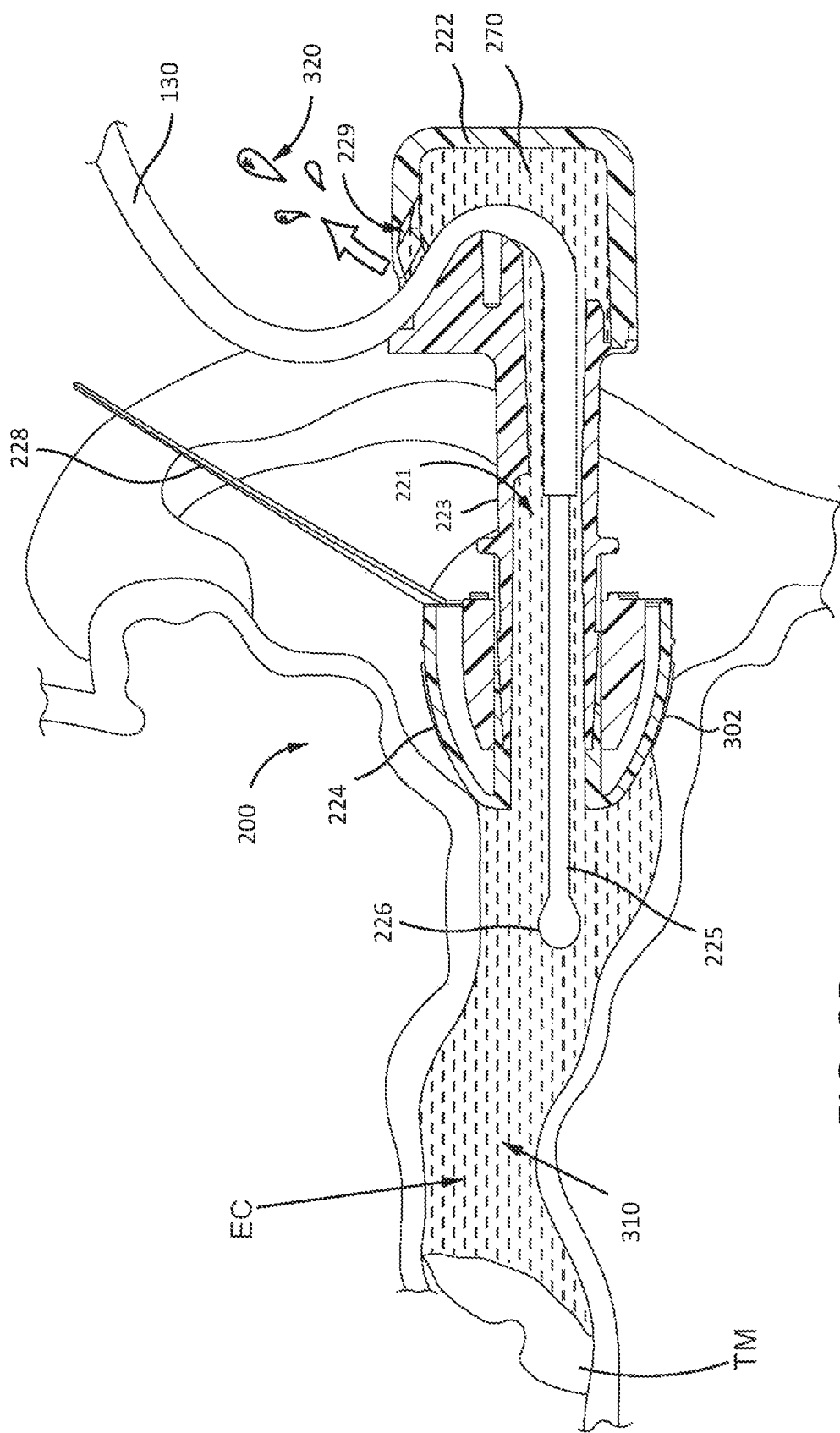
FIG. 3B depicts another cross-sectional view of the earset of FIGS. 2A and 2B, with an ear canal of the ear filled with a fluid and some fluid escaping through a vent path of the earset, in accordance with some embodiments.
Figure 3C:
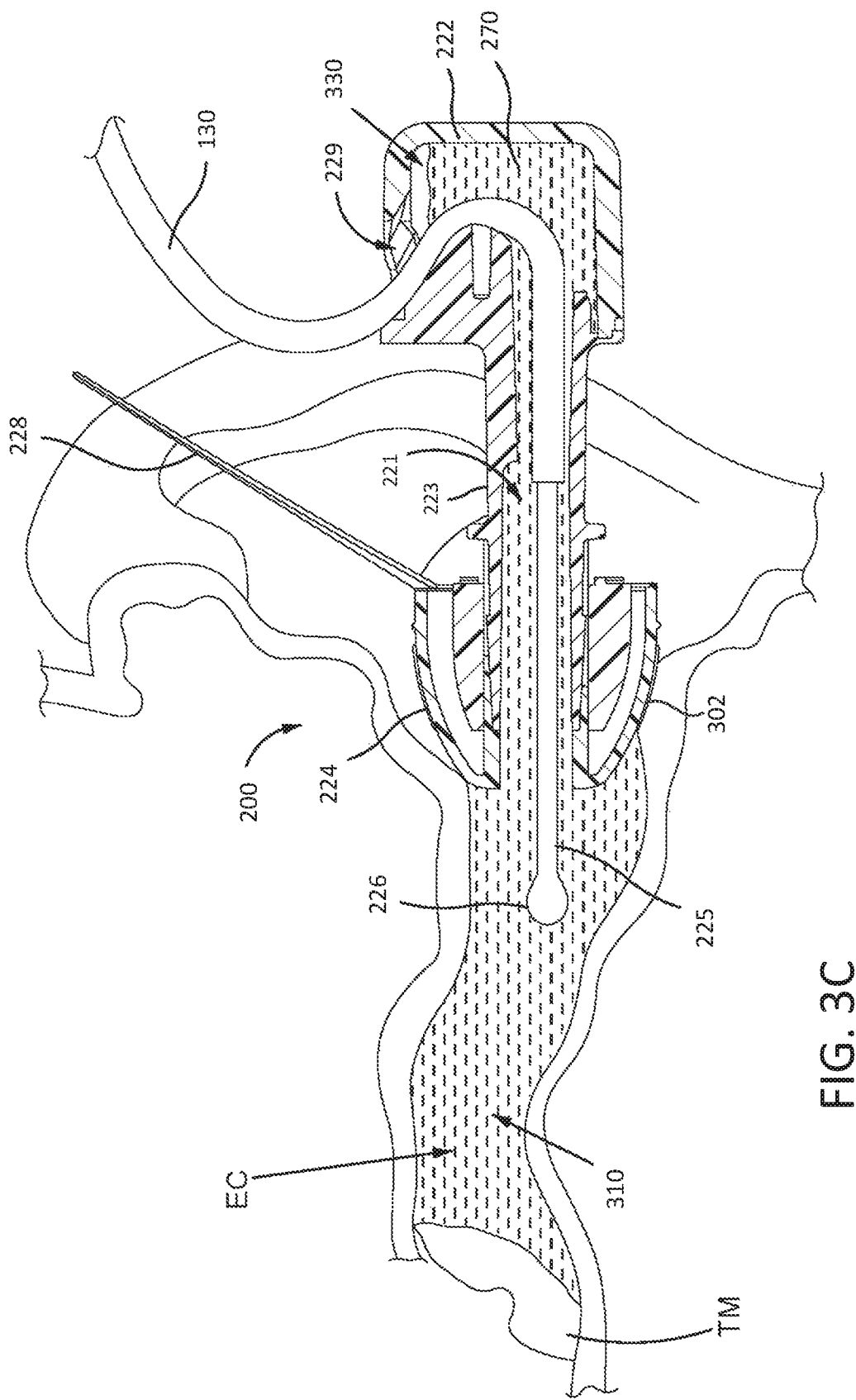
FIG. 3C depicts another cross-sectional view of the earset of FIGS. 2A and 2B, with an ear canal of the ear filled with a fluid and a bubble formed in the fluid, in accordance with some embodiments.

FIGS. 3A-3C illustrate earset 200 being used in an iontophoresis procedure. As shown in FIG. 3A, earset 200 can be positioned in an ear canal EC of a subject. Sealing element 224 is positioned such that it bears against a surface of the ear canal EC. Sealing element 224 can secure earset 200 to the ear and form a fluid seal against a surface of ear canal EC. The sealing of the ear canal EC creates a cavity between tympanic membrane TM and earset 200 that can receive iontophoresis fluid. In some embodiments, a pressure sensitive adhesive can be disposed on sealing element 224. A liner strip 220 (as shown in FIG. 1) can cover the pressure sensitive adhesive during placement of the earset 200 in the ear canal EC. The liner strip 220 can be removed to expose the pressure sensitive adhesive such that the pressure sensitive adhesive can adhere to the surface of the ear canal EC, further ensuring that the earset 200 remains secured to the ear canal EC and that a fluid seal is formed between the flexible sealing element 224 and the ear canal EC.

Once earset 200 is secured in the ear canal EC, a user can begin administration of iontophoresis fluid into the ear canal EC via nozzle 226. The user can connect fluid source 140 to conduit 130 and use fluid source 140 to supply the iontophoresis fluid. As the iontophoresis fluid is supplied, the ear canal EC, working channel 221, and reservoir 270 can fill with fluid, and the air displaced from the ear canal EC, working channel 221, and reservoir 270 will flow out to an exterior of the earset 200 through vent path 229. The user can continue to supply the iontophoresis fluid until fluid 320 is observed flowing out through vent path 229, as shown in FIG. 3B. The fluid 320 flowing out through vent path 229 signifies to the user that the ear canal EC, working channel 221, and reservoir 270 are full of the iontophoresis fluid and that the electrode 252 can be activated. In some embodiments, gripping feature 222 can be transparent to enable a user to observe reservoir 270 filling with the iontophoresis fluid.

Prior to activating the electrode 252, the user can remove the fluid source 140. In some instances, removal of the fluid source 140 can result in a loss of iontophoresis fluid from working channel 221 and reservoir 270. For example, removal of the fluid source 140 can result in a loss of 0.04 cc or milliliters of iontophoresis fluid. As a result, an air pocket 330 of a corresponding volume may form in reservoir 270, as shown in FIG. 3C. Due to the shape of reservoir 270, air pocket 330 is spaced away from iontophoresis electrode 252 such that iontophoresis electrode 252 remains fully submerged in the iontophoresis fluid.

In some instances, fluid can escape from reservoir 270 before and/or during an iontophoresis procedure. Oftentimes, fluid can escape before an iontophoresis procedure either via vent path 229 or due to a non-ideal fit of the earset 200 in the ear canal (e.g., when flexible sealing element 224 does not form a fluid-tight seal against a surface of the ear canal). For example, movement by a subject (e.g., as a result of coughing, talking, swallowing, crying, yawning, or otherwise) can cause variation in the volume of the ear canal EC. Such volumetric changes can cause a pumping action, which can lead to changes in the level of iontophoresis fluid within reservoir 270. In some instances, the volumetric changes can cause iontophoresis fluid to displace out of vent path 229. The reduction in iontophoresis fluid correspondingly causes the air pocket 330 in reservoir 270 to expand and contract. Because of the volume and L-shaped configuration of reservoir 270, the air pocket 330 may remain in reservoir 270 spaced from the working channel 221 and therefore the electrode 252. The air pocket 330 therefore does not affect the operation of electrode 252 and would not impact an iontophoresis procedure.

Figure 4:
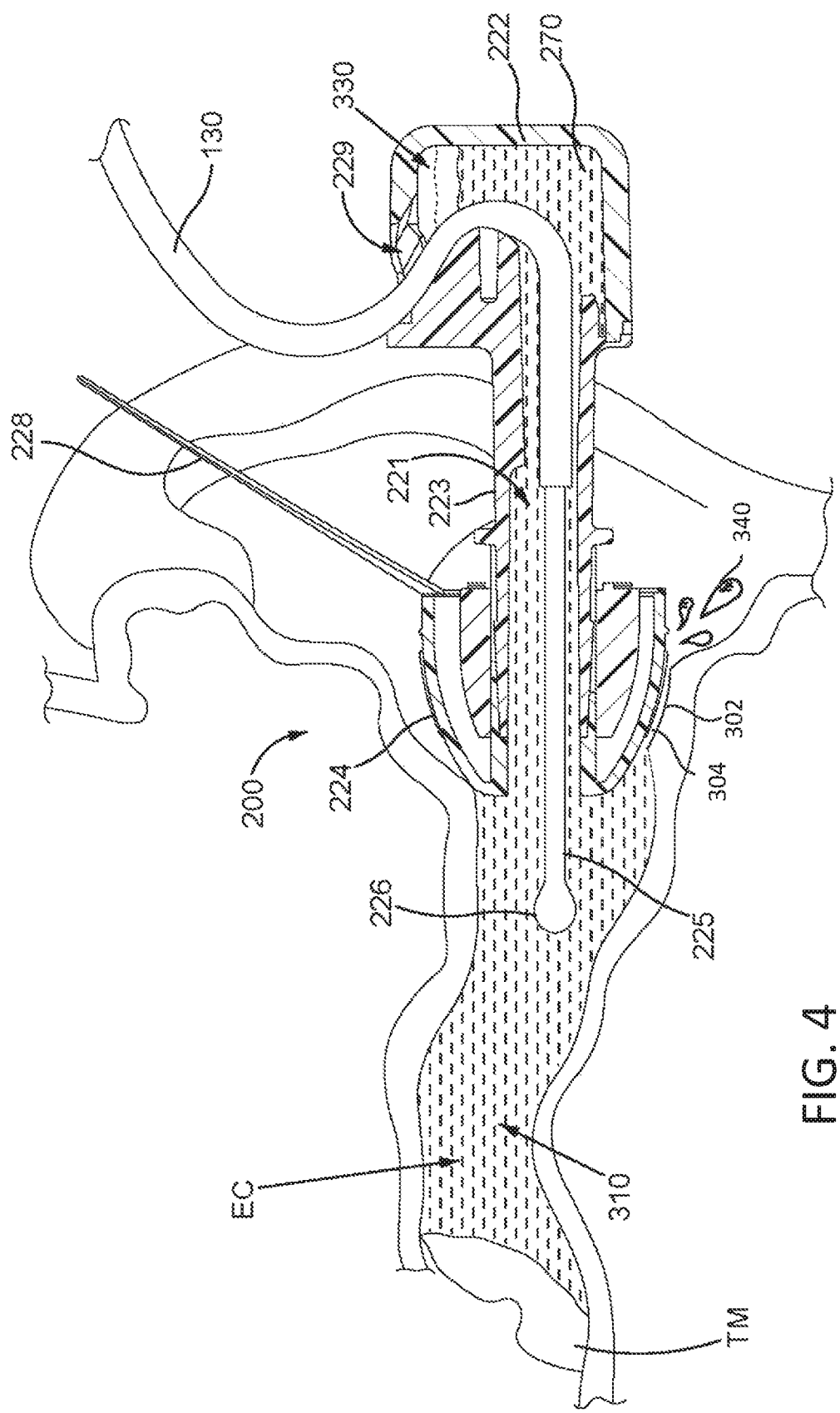
FIG. 4 depicts another cross-sectional view of the earset of FIGS. 2A and 2B, with an ear canal of the ear filled with a fluid and a fluid leak between a surface of the ear and the earset, in accordance with some embodiments.

In some instances, however, a leak may form between a surface of ear canal EC and flexible sealing element 224. When a leak forms between a surface of ear canal EC and flexible sealing element 224, iontophoresis fluid from within ear canal EC, working channel 221, and reservoir 270 may leak out, which can interrupt an iontophoresis procedure. For example, as shown in FIG. 4, a gap or opening 304 can form between flexible sealing element 224 and a surface 302 of ear canal EC. Gap 304 can form when a physician or the patient pushes or pulls on part of the earset 200 (e.g., when adjusting the earset 200), from the patient's movements (e.g., talking, crying, yawning, eating, or moving his jaw), or due to a non-ideal fit of earset 200 within ear canal (e.g., when flexible sealing element 224 does not form a fluid-tight seal against a surface of the ear canal EC). The gap 304 can form before or during an iontophoresis procedure. When gap 304 forms, iontophoresis fluid can leak out of gap 304 and be replaced with air that flows into the reservoir 270 via vent path 229. As the iontophoresis fluid leaks out of gap 304, the size of air pocket 330 can increase, as shown in FIG. 4. In some instances, an air pocket or bubble can also migrate to a surface of iontophoresis electrode 252. If the leak is not resolved, then iontophoresis fluid may continue to leak out of the ear canal EC until iontophoresis electrode 252 becomes exposed to air, e.g., due to an increase in the size of air pocket 330 or a migration of an air pocket to a surface of iontophoresis electrode 252. Such exposure to air can cause a delay or interruption of the iontophoresis procedure. Before the iontophoresis procedure can begin or resume, the leak would need to be resolved (e.g., the gap 304 would need to be plugged such that fluid can no longer leak out of reservoir 270) and the reservoir 270 refilled with iontophoresis fluid. In some instances, earset 200 may need to be replaced with a new earset that can form a new fluid seal against a surface of ear canal EC. The added effort of resolving the leak and/or replacing the earset 200 can extend the amount of time required for the iontophoresis procedure and require additional interaction or contact between a physician and a patient. The extended time and/or additional contact between the physician and patient can cause discomfort, frustration, and impatience, potentially leading to behavioral challenges, especially in younger patients.

To provide some resistance to fluid leakage, vent path 229 and/or other openings in earset 200 that allow for the entry of air into earset 200 can be closed such that air does not readily displace fluid that leaks out through gap 304. In an embodiment, a user can manually close vent path 229 to prevent air from entering earset 200 and displacing fluid that leaks out through gap 304. For example, the user may use his finger to cover vent path 229, or the user can use a plug, tape, or another mechanism to close the vent path 229. The user can keep the vent path 229 closed until the iontophoresis procedure is completed and/or until the gap 304 is plugged. In some instances, however, it can be difficult for a user to close the vent path 229 and/or to keep the vent path 229 closed. For example, the vent path 229 can be positioned on the earset 200 in a location that is difficult for a user to access, or the vent path 229 may have a size and/or configuration that makes it difficult for a user to close (e.g., the vent path 229 may be formed in a concavity). In some embodiments, vent path 229 may be sized and/or configured to prevent it from being easily closed or blocked because it is undesirable for vent path 229 to be covered when earset 200 is being filled with iontophoresis fluid. For instance, if vent path 229 became blocked when earset 200 is being filled with iontophoresis fluid, then pressure could build up within the ear canal EC and cause patient discomfort and/or injury.

Figure 5:
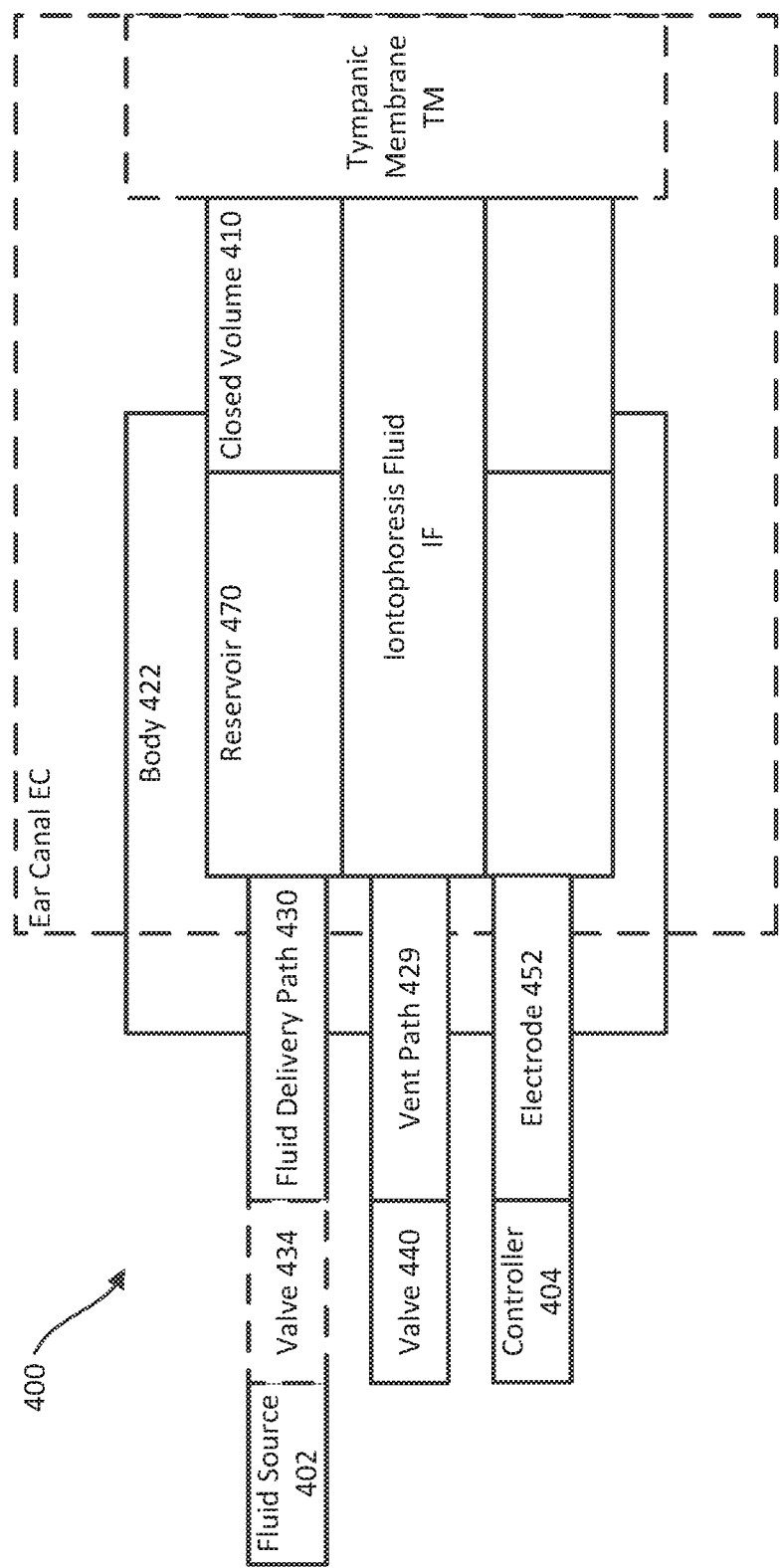
FIG. 5 is a schematic illustration of another example of an iontophoresis system, in accordance with some embodiments.

In some embodiments, a valve can be used to prevent air from entering an earset (e.g., earset 200) via a vent path. The valve can allow air to exit the earset when the earset is being filled with a fluid but prevent air from flowing back into the earset when a leak develops. As schematically shown in FIG. 5, an iontophoresis system 400 can include a valve 440. Valve 440 can limit the flow of a fluid (e.g., air and/or liquid) through a vent path 429. In some embodiments, iontophoresis system 400 can optionally include an additional valve 434 that can control the flow of a fluid (e.g., iontophoresis fluid) between a fluid source 402 and a reservoir 470 of iontophoresis system 400.

Similar to iontophoresis system 100, iontophoresis system 400 can include an iontophoresis electrode 452, a reservoir 470, a vent path 429, a fluid source 402, and a controller or control unit 404.

Iontophoresis system 400 can be positioned within an ear canal EC of a subject. Specifically, a portion of a body 422 of iontophoresis system 400 can be positioned within the ear canal EC. The body 422 of iontophoresis system 400 can include one or more rigid, semi-rigid, or flexible components. For example, body 422 can include a flexible sealing element similar to flexible sealing element 224 of iontophoresis system 100 that can secure iontophoresis system 400 to ear canal EC and form a seal with a surface of ear canal EC. In some embodiments, a pressure sensitive adhesive can also be disposed on the flexible sealing element to help secure iontophoresis system 400 to ear canal EC. When iontophoresis system 400 is secured to ear canal EC, a portion of body 422 (e.g., flexible sealing element) can define a closed volume 410 within ear canal EC outside of a tympanic membrane TM.

Body 422 defines the reservoir 470, which can receive iontophoresis fluid IF. Reservoir 470 is in fluid communication with closed volume 410. Electrode 452 can be used to supply an electric current to iontophoresis fluid IF to drive drug ions within iontophoresis fluid IF into tympanic membrane TM. Electrode 452 can be coupled to or separate from but engageable with reservoir 470. In some embodiments, electrode 452 can be disposed within body 422 within and/or adjacent to reservoir 470. Electrode 452 can have any general shape (e.g., coiled wire, straight wire, mesh, etc.).

In some embodiments, electrode 452 can have different configurations to increase surface area and promote iontophoresis. For example, electrode 452 can include one or more of: a plurality of wires configured similar to a brush head, a plurality of concentric tubes with staggered diameters that are nested within one another, a silver mesh mass configured similar to steel wool, a molded polymer matrix plug with a sponge-like structure and a metal plating or deposition (e.g., a pure silver plating or deposition), a metal-coated woven fabric, a honeycomb structure, a coil structure, a mass with a plurality of petals or branches (e.g., flower shaped), a flexible bag structure, one or more cavities or recesses with metal-coated surfaces, a textured surface (e.g., cross-hatched, etched, sandblasted), a laser-cut tube with cavities or recesses, etc. In some embodiments, electrode 452 can be coupled to a controller 404 that supplies power to electrode 452 and controls when electrode 452 applies a current to iontophoresis fluid IF. The controller can include safety features that prevent the electrode 452 from activating and applying a current until iontophoresis system 400 is properly positioned within ear canal EC and is filled with iontophoresis fluid IF. For example, electrode 452 can include a sensor that informs the controller 404 of when electrode 452 is submerged within iontophoresis fluid IF before allowing a user to actuate the controller 404 and apply an electric current.

In some embodiments, electrode 452 can include multiple metals with one metal (e.g., zinc) serving as a galvanic or sacrificial anode. In some embodiments, electrode 452 can include a conveyor system (e.g., a flexible belt) that can be actuated to supply a fresh electrode surface during an iontophoresis procedure. In some embodiments, electrode 452 can include wiping or cleaning mechanisms that can be actuated to clean the surface of electrode 452. In some embodiments, electrode 452 can include a protective coating to help prevent corrosion.

Valve 440 can be a one-way valve. Valve 440 can be configured to limit fluid flow through vent path 429. In some embodiments, valve 440 can be a flow control valve, i.e., a valve that provides a substantially constant flow regardless of the pressure drop through the valve. In other embodiments, valve 440 can be a pressure control valve, i.e., a valve that opens and/or closes above a predetermined pressure threshold.

As depicted, valve 440 can be disposed in vent path 429. In other embodiments, valve 440 can be disposed adjacent or proximate to vent path 429. Valve 440 can be configured to allow fluid (e.g., air and/or liquid) to flow out of reservoir 470 with low resistance but limit fluid (e.g., air and/or liquid) from flowing into reservoir 470. In particular, during use of iontophoresis system 400, valve 440 can be configured to allow air and/or excess iontophoresis fluid IF to flow out of reservoir 470 such that pressure does not build up within reservoir 470 when reservoir 470 is being filled with iontophoresis fluid IF. Valve 440 can also be configured to limit the flow of air (or other fluid substances) back into reservoir 470. Valve 440 can be an umbrella valve, or any other suitable type of valve that can limit fluid flow in one direction (e.g., a duckbill valve, a dome valve, a seated valve, a ball check valve). Valve 440 can reduce fluid leaks out of reservoir 470 and/or ear canal EC by preventing air from flowing into reservoir 470 and displacing fluid that has leaked out of reservoir 470 and/or ear canal EC.

In some embodiments, valve 440 can be designed to provide negative pressure relief. For example, valve 440 can be designed to open when a pressure drop through the valve is greater that a preset level. Valve 440 can prevent fluid (e.g., air and/or liquid) from flowing into reservoir 470 unless and/or until the pressure within reservoir 470 is below a certain gauge pressure, thereby allowing fluid to flow into reservoir 470. By allowing fluid to flow into reservoir 470, valve 440 can relieve negative pressure within reservoir 470 and reduce patient discomfort caused by the negative pressure. Negative pressure may build up within reservoir 470 when a physician inadvertently applies suction via a syringe (e.g., a fluid source) connected to fluid delivery path 430. To prevent the patient from experiencing discomfort due to the applied suction, valve 440 can be designed to fail and allow fluid to enter reservoir 470 before the pressure reaches a threshold for discomfort, e.g., −1 kPa.

In some embodiments, iontophoresis system optionally includes a second valve, e.g., valve 434. Valve 434 can be disposed between fluid source 402 and fluid delivery path 430, or be disposed at a point along fluid delivery path 430. Valve 434 can be designed to allow fluid (e.g., iontophoresis fluid IF) to flow from fluid source 402 in the direction of reservoir 470 but prevent fluid from flowing back toward fluid source 402. When fluid source 402 is a syringe, valve 434 prevents a physician from applying a suction via the syringe, thereby avoiding negative pressure within reservoir 470. Similar to valve 440, valve 434 can be a one-way valve.

Figure 6:
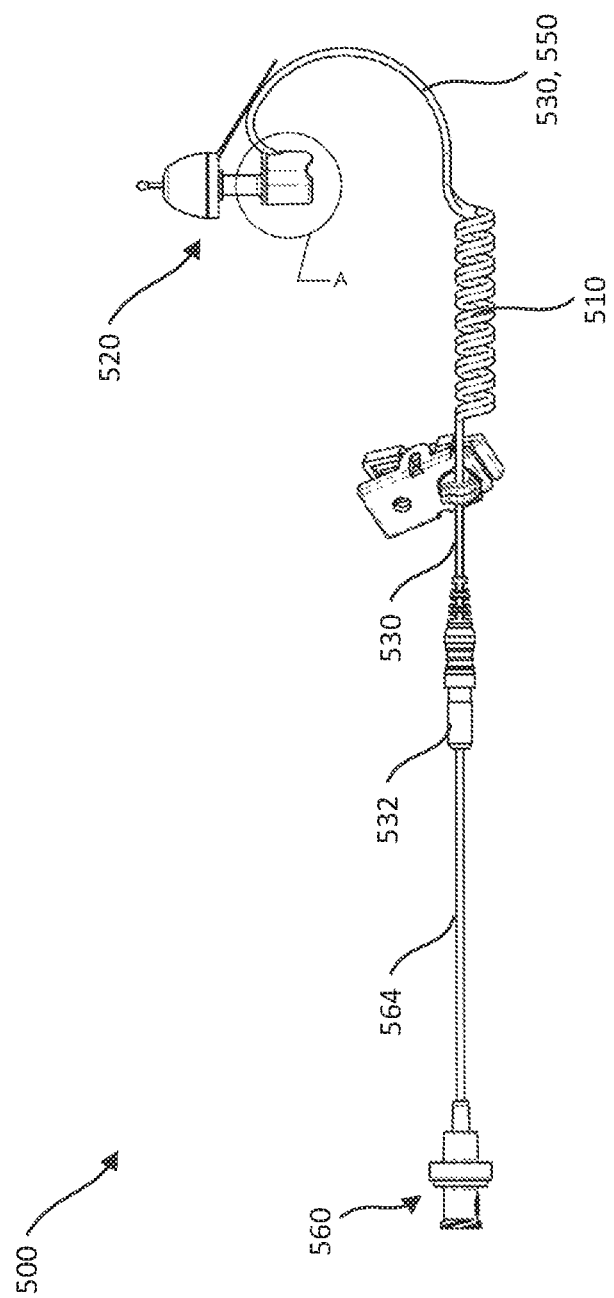
FIG. 6 depicts a perspective view of another example iontophoresis system including an earset, in accordance with some embodiments.
Figure 7A:
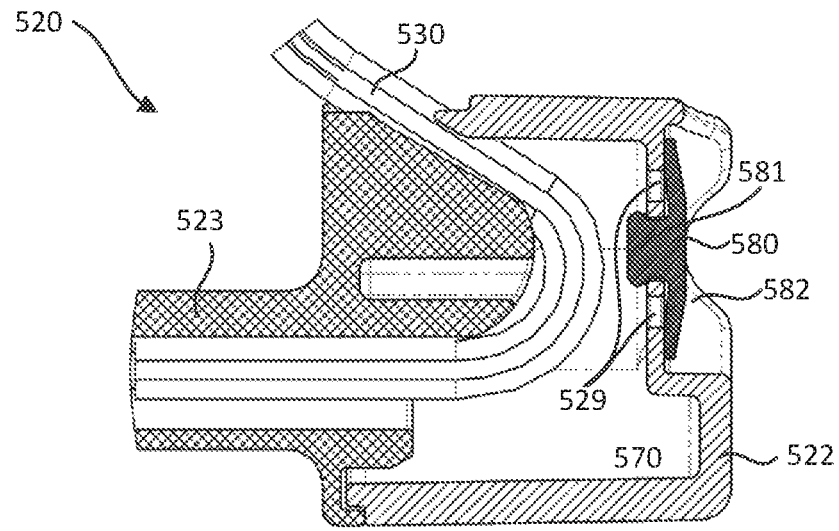
FIGS. 7A and 7B depict cross-sectional views of the earset of the iontophoresis system of FIG. 6, with a one-way valve positioned in a vent path of the earset, in accordance with some embodiments.
Figure 7B:
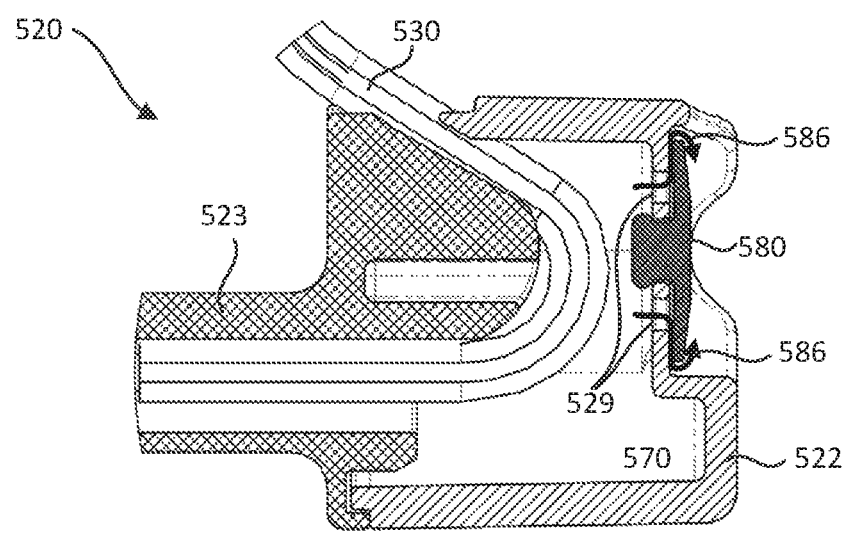

FIG. 6 depicts an example of an iontophoresis system including a valve. In particular, iontophoresis system 500 includes components that are similar to iontophoresis system 100 but also includes a one-way valve 580 (depicted in FIGS. 7A-8B). Iontophoresis system 500 includes an earset 520. Earset 520 is in communication with a fluid source (not shown) via one or more connectors (e.g., connector 532) and conduits (e.g., conduits 530, 564). Earset 520 is also in communication with a control unit (not shown) and a ground pad (not shown) via a connector and a cable 550. Conduit 530 and cable 550 can be coupled together along a shared length extending between earset 520 and a clip. A portion 510 of the shared length of the conduit 530 and cable 550 can be coiled such that it can be expanded and/or contracted to adjust the distance between the clip and earset 520.

Iontophoresis system 500 can include an adapter 560. Adapter 560 can be connected to a fluid source such as, for example, a syringe 540 (shown in FIG. 10). As described in further detail below with reference to FIGS. 10, 11A, and 11B, adapter 560 can include a valve for controlling the flow of a fluid from the fluid source. Adapter 560 can be connected to connector 532 via a conduit 564. Conduit 564 together with conduit 530 can provide a path for delivering fluid from the fluid source to earset 520.

While one earset 520 is shown in FIG. 6, it should be understood that iontophoresis system 500 can have two earsets 520 that can be used in both ears of a subject to provide simultaneous and/or sequential delivery of a therapeutic substance via iontophoresis.

FIGS. 7A, 7B, 8A, and 8B show cross-sectional views of a portion of earset 520 within a region A circled in FIG. 6. Earset 520 includes housing portions 522, 523. Housing portions 522, 523 can cooperate to define a reservoir 570. Reservoir 570 is in fluid communication with conduit 530 such that a fluid, such as, for example, iontophoresis fluid, can be delivered to reservoir 570 via conduit 530. Housing portion 522 can define a gripping feature, which can be gripped by a user and serve as a handle during insertion of earset 520 into an ear of a subject.

As depicted, earset 520 includes an umbrella valve 580. In other embodiments, earset 520 can include a different type of valve, such as a duckbill valve, a dome valve, a seated valve, or a ball check valve. Valve 520 can be formed of a flexible material such as, for example, an elastomer. Valve 520 can be configured to limit flow through one or more vent paths 529. Vent paths 529 can be formed as openings in housing portion 522. In other embodiments, vent paths 529 can have different sizes and/or configurations. In some embodiments, valve 520 can be releasably coupled to housing portion 522. For example, valve 520 can include a portion 518 (depicted in FIG. 7A) that can be inserted into an opening in housing portion 522. Portion 518 of valve 520 can be sized to retain the coupling between valve 520 and housing portion 522. Portion 518 of valve 520 can deform when it is inserted into housing portion 522 and then revert back to its resting configuration to retain portion 518 in housing portion 522. In other embodiments, housing portion 522 can be permanently attached to or integrally formed with housing portion 522.

During an iontophoresis operation, a fluid source (e.g., syringe 540) can be used to fill reservoir 570 with an iontophoresis fluid. Valve 580 can be configured to allow air from within reservoir 570 to flow out of reservoir 570 via vent paths 529 and one or more openings 584 (shown in FIG. 9) when reservoir 570 is being filled with iontophoresis fluid. For example, in response to a slight positive pressure increase within reservoir 570, an umbrella portion of valve 580 can move and uncover vent paths 529, thereby allowing air to flow out of reservoir 570 as shown by arrows 586 in FIG. 7B.

Figure 8A:
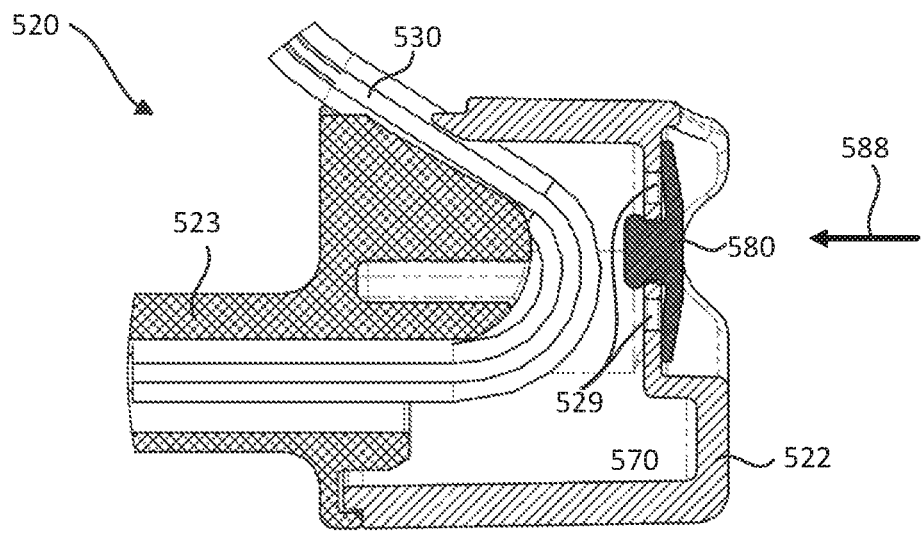
FIGS. 8A and 8B depict additional cross-sectional views of the earset of the iontophoresis system of FIG. 6, with a valve positioned in a vent path of the earset, in accordance with some embodiments.

Valve 580 is further configured to prevent air or another gas and/or liquid from flowing back into reservoir 570. For example, as shown in FIG. 8A, when a slight negative pressure builds within reservoir 570 and/or a positive pressure acts in a direction 588 on valve 580, the umbrella portion of valve 580 closes down on vent paths 529 such that air from outside of earset 520 is prevented from flowing into reservoir 570 via vent paths 529. By preventing air from flowing back into reservoir 570, valve 580 can reduce fluid leaks. For example, when a gap develops such that iontophoresis fluid from within the ear and/or reservoir 570 can leak out via the gap, valve 580 can prevent air from flowing into reservoir 570 such that the air does not readily displace any fluid that leaks out through the gap. As such, valve 580 can provide a degree of resistance to a fluid leak by limiting the flow of fluid into reservoir 570.

Figure 8B:
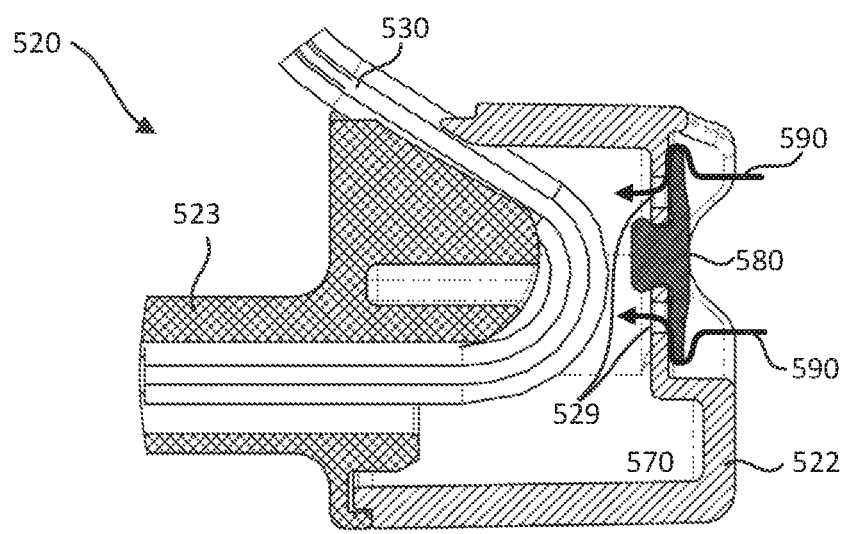

In some embodiments, valve 580 can be configured to provide negative pressure relief such as, for example, when a suction is applied (e.g., inadvertently by a physician) to reservoir 570 by a fluid source (e.g., syringe 540) connected to conduit 530 by, for example, a physician. The suction can cause a negative pressure to build within reservoir 570. At a certain level, the negative pressure may cause patient discomfort and/or injury. Therefore, to prevent discomfort and/or injury, valve 580 can be designed to open or fail when the gauge pressure within reservoir 570 is below a certain pressure threshold to allow air to enter reservoir 570, thereby reducing the negative pressure within reservoir 570. As depicted in FIG. 8B, when valve 580 fails, the umbrella portion of valve 580 can flare outward, uncovering vent paths 529 to allow air to enter reservoir 570 as shown by arrows 590 (depicted in FIG. 8B). In an embodiment, valve 580 can be designed to fail above a negative gauge pressure of 1 kPa or when a difference in pressure or differential pressure between an inside of earset 520 (i.e., a pressure within reservoir 570) and an exterior of earset 520 is greater than 1 kPa.

As shown in FIGS. 7A-8B, valve 580 and vent paths 529 can be disposed within a concavity 582 defined in earset 520. Concavity 582 can reduce the risk of a user accidentally covering one or more openings 584, which could compromise the operation of vent paths 529. Multiple openings 584 can also be provided to reduce the risk that the operation of vent paths 529 could be compromised.

Figure 9:
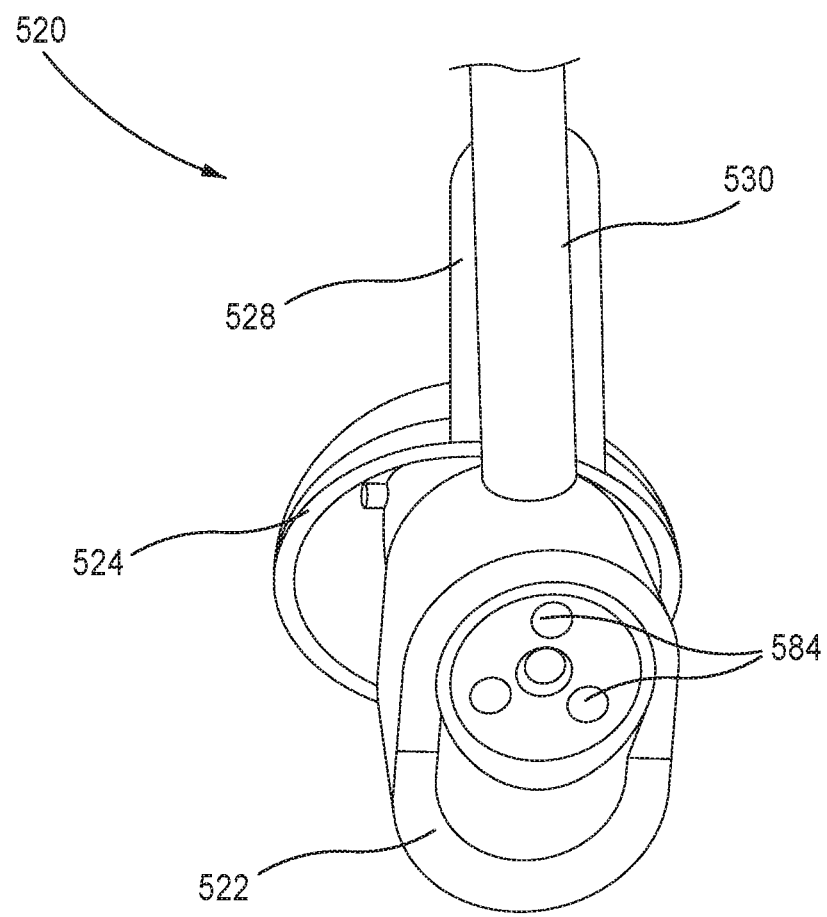
FIG. 9 depicts a side, perspective view of the earset of the iontophoresis system of FIG. 6, showing one or more vent paths disposed below the valve of the earset, in accordance with some embodiments.

FIG. 9 depicts a backside view of earset 520. As shown, earset 520, similar to earset 200 described above, includes a retrieval element such as a pull-tab 528 and a flexible sealing element 524.

In some embodiments, earset 520 can include a valve that defines the vent path. In such embodiments, separate vent paths formed in a housing of the earset 520 (e.g., vent paths 529 as shown in FIGS. 7A-8B) may not be necessary. The valve can include a post or ball and a seating element (e.g., a seating ring or disc), where the seating element includes an opening that functions as the vent path and the post or ball is configured to close the opening to prevent fluid from flowing into earset 520. In other embodiments, earset 520 can include an electrically actuated component that operates as a one-way valve.

Figure 10:
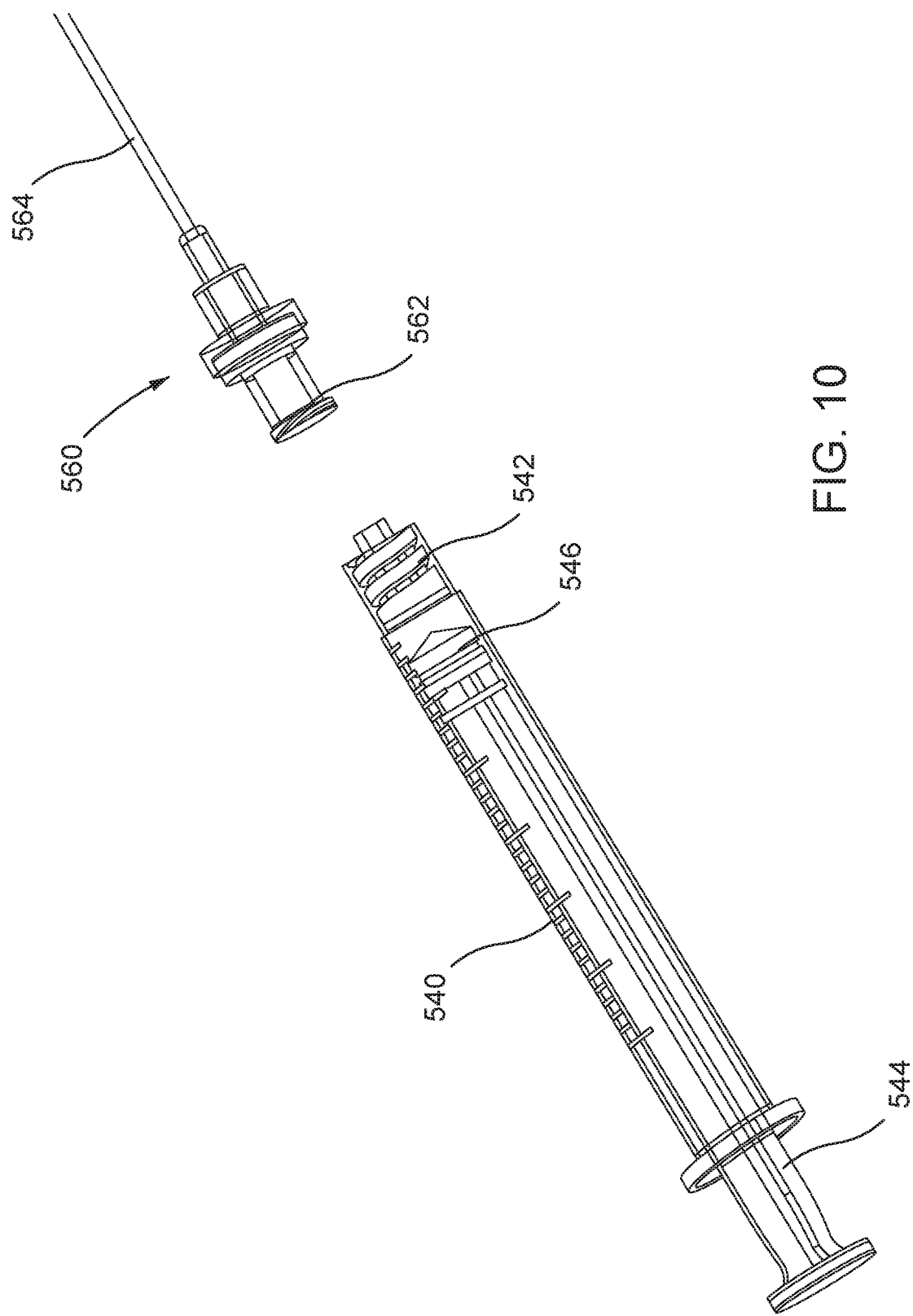
FIG. 10 depicts an example of a fluid source adapter for use in an iontophoresis system, in accordance with some embodiments.
Figure 11A:
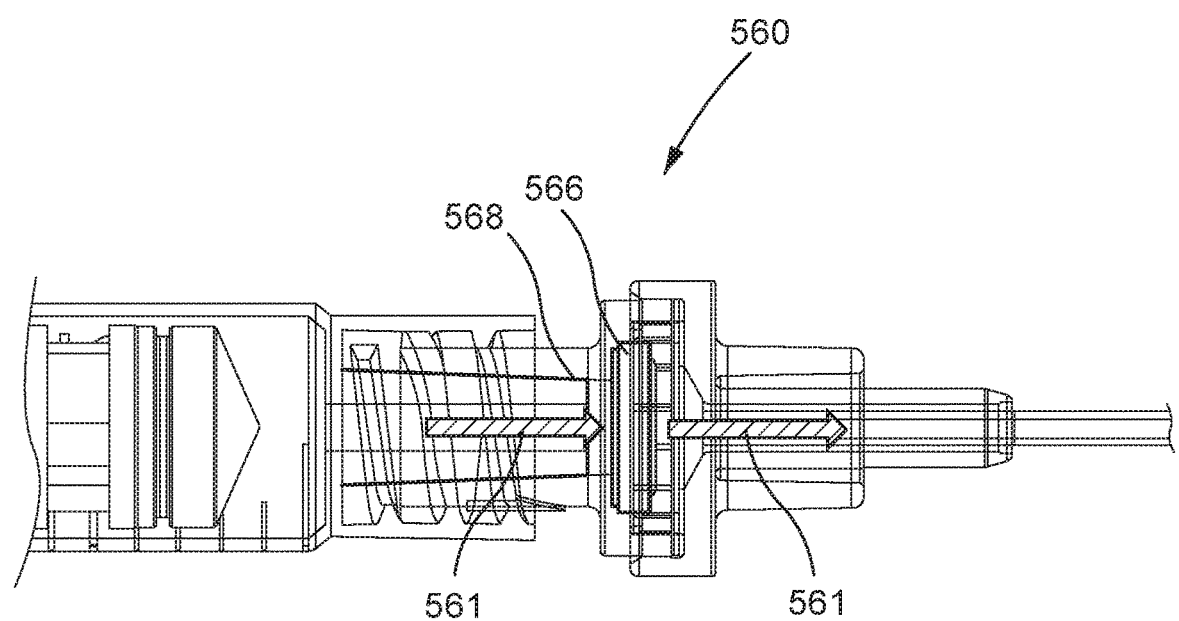
FIGS. 11A and 11B depicts cross-sectional views of the fluid source adapter of FIG. 10, with a one-way valve component, in accordance with some embodiments.
Figure 11B:
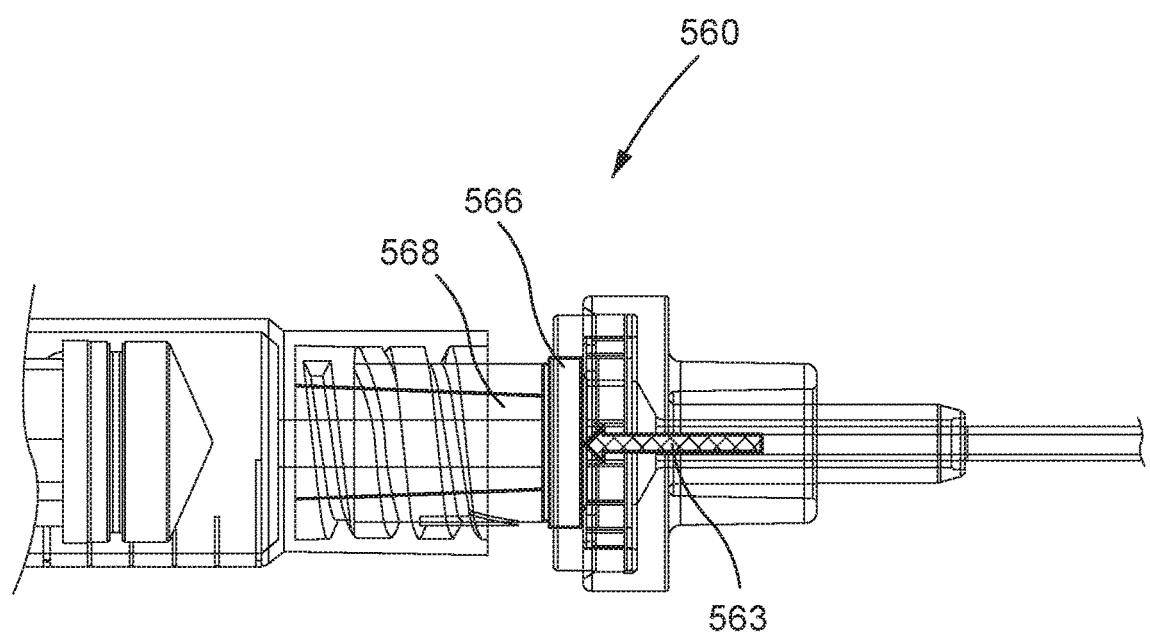

FIGS. 10, 11A, and 11B provide more detailed views of adapter 560. FIG. 10 provides a perspective view of adapter 560 with a syringe 540 that can be coupled to adapter 560.

FIGS. 11A and 11B provide cross-sectional views of adapter 560. Adapter 560 can be connected to conduit 564, which can connect to one or more other conduits (e.g., conduit 530) to provide a fluid flow path between syringe 540 and reservoir 570. Syringe 540 can be used to supply an iontophoresis fluid to reservoir 570. Syringe 540 can be similar to a standard syringe, and can include a shaft 544 with a plunger 546 that is disposed within a barrel 540. Syringe 540 can be releasably coupled via its Luer tip 542 to an end 562 of adapter 560. End 562 of adapter 560 can be shaped to receive and mate with the Luer tip 542 of syringe 540. While a syringe 540 with a Luer tip 542 and an adapter 560 with an end 562 shaped to engage a Luer tip are shown, one of ordinary skill in the art would understand that other types of connections between a syringe or other type of fluid source and an adapter can be used.

Adapter 560 can include a valve 566. Valve 566 can allow a fluid (e.g., iontophoresis fluid) to flow in a first direction 561 out of syringe 540 but prevent the fluid from flowing in a second, opposite direction 563 back toward syringe 540. As depicted in FIGS. 11A and 11B, valve 566 can be formed of a disk that can move between an open position (FIG. 11A) and a seated position (FIG. 11B). When valve 566 is in the open position, valve 566 is separated from a seating post 568 such that fluid from within syringe 540 can flow out of syringe 540. And when valve 466 is in the seated position, valve 566 can be seated against seating post 568 such that fluid cannot flow back toward syringe 540. By preventing backflow of fluid toward syringe 540, valve 566 can prevent suction from being applied by syringe 540 to reservoir 570, thereby reducing the risk of negative pressure buildup within reservoir 570. With the addition of valve 580 to earset 520, a physician can inadvertently generate negative pressure within reservoir 570 and the ear canal if the physician retracts the syringe 540. As described above, valve 580 can be designed to fail to reduce negative pressure within earset 520. As an additional or alternative measure, valve 566 can be used to prevent negative pressure from generating within reservoir 570 due to the addition of valve 580.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The invention claimed is:

1. An apparatus, comprising:
   a body defining a channel and a reservoir in fluid communication with the channel;
   an electrode disposed within the channel; and
   a valve disposed through a wall of the reservoir, the valve configured to: (i) allow a fluid to flow from within the reservoir to an exterior of the apparatus through the valve, and (ii) prevent the fluid from entering the reservoir from the exterior of the apparatus through the valve.

2. The apparatus of claim 1, further comprising a sealing element disposed at a distal end of the body, the sealing element configured to form a seal against a surface of an ear canal of an ear to define a closed volume between a tympanic membrane of the ear and the apparatus in fluid communication with the channel.

3. The apparatus of claim 2, wherein the fluid is a first fluid, and further comprising a fluid conduit in fluid communication with at least one of the channel and the reservoir and configured to fill the channel, the reservoir, and the closed volume with a second fluid, the valve further configured to allow the second fluid to flow from within the reservoir to the exterior of the apparatus through the valve.

4. The apparatus of claim 3, wherein the electrode is submerged in the second fluid after the fluid conduit fills the channel with the second fluid.

5. The apparatus of claim 3, wherein the first fluid is atmospheric air, and the second fluid is an iontophoresis fluid including a therapeutic substance.

6. The apparatus of claim 1, wherein the valve is an umbrella valve.

7. The apparatus of claim 1, wherein the fluid is atmospheric air.

8. An apparatus, comprising:
   a body defining a channel and a reservoir in fluid communication with the channel;
   an electrode disposed within the channel; and
   a valve disposed at a portion of the body defining the reservoir, the valve configured to:
   (i) allow a fluid to flow from within the reservoir to an exterior of the apparatus through the valve in response to a positive gauge pressure within the reservoir; and
   (ii) prevent the fluid from entering the reservoir from the exterior of the apparatus through the valve when a differential pressure between an interior of the reservoir and the exterior of the apparatus is less than a predefined value.

9. The apparatus of claim 8, wherein the valve is further configured to (iii) allow the fluid to enter the reservoir from the exterior of the apparatus through the valve when the differential pressure is greater than the predefined value being 1 kPa.

10. The apparatus of claim 8, wherein the valve is a first valve and the fluid is a first fluid, and further comprising:
    a fluid conduit in fluid communication with at least one of the channel and the reservoir and configured to fill the channel and the reservoir with a second fluid;
    a connector disposed at a proximal end of the fluid conduit and configured to connect to a fluid source providing the second fluid;
    a second valve disposed in one of the connector or the fluid conduit and configured to: (i) allow the second fluid to flow in a first direction toward the at least one of the channel and the reservoir, and (ii) prevent the second fluid from flowing in a second direction opposite to the first direction.

11. The apparatus of claim 8, further comprising a sealing element disposed at a distal end of the body, the sealing element configured to form a seal against a surface of an ear canal of an ear to define a closed volume between a tympanic membrane of the ear and the apparatus.

12. The apparatus of claim 11, wherein the fluid is a first fluid, and further comprising a fluid conduit in fluid communication with at least one of the channel and the reservoir and configured to fill the channel, the reservoir, and the closed volume with a second fluid, the valve further configured to allow the second fluid to flow from within the reservoir to the exterior of the apparatus.

13. The apparatus of claim 12, wherein the electrode is submerged in the second fluid after the fluid conduit fills the channel with the second fluid.

14. The apparatus of claim 12, wherein the first fluid is atmospheric air, and the second fluid is an iontophoresis fluid including a therapeutic substance.

15. The apparatus of claim 8, wherein the valve is an umbrella valve.

16. The apparatus of claim 8, wherein the fluid is atmospheric air.

17. An apparatus, comprising:
    a body defining a channel and a reservoir in fluid communication with the channel;
    a sealing element disposed at a distal end of the body, the sealing element configured to form a seal against a surface of an ear canal of an ear to define a closed volume between a tympanic membrane of the ear and the apparatus;
    a fluid conduit in fluid communication with at least one of the channel and the reservoir and configured to fill the channel, the reservoir, and the closed volume with a first fluid;
    an electrode disposed within the channel, the electrode is configured to be submerged in the first fluid after the fluid conduit fills the channel with the first fluid;
    the reservoir is configured to contain a pocket of a second fluid in a space separated from the electrode, the channel configured to maintain the submersion of the electrode in the first fluid when the pocket of the second fluid is in the reservoir;
    a vent path in fluid communication with the reservoir; and
    a valve disposed in the vent path and configured to:
    (i) allow the first fluid to flow from within the reservoir to an exterior of the apparatus in response to a positive gauge pressure within the reservoir;
    (ii) prevent the second fluid from entering the reservoir from the exterior of the apparatus when a differential pressure between an interior of the reservoir and the exterior of the apparatus is less than a predefined value; and
    (iii) allow the second fluid to enter the reservoir from the exterior of the apparatus when the differential pressure is greater than the predefined value.

18. An apparatus, comprising:
an earset including:
- a body defining a channel and a reservoir in fluid communication with the channel;
- a vent path in fluid communication with the reservoir; and
- a first valve disposed in the vent path and configured to: (i) allow a first fluid to flow from within the reservoir to an exterior of the apparatus, and (ii) prevent the first fluid from entering the reservoir from the exterior of the apparatus;
- a fluid conduit in fluid communication with at least one of the channel and the reservoir and configured to fill the channel and the reservoir with a second fluid;
- a connector disposed at a proximal end of the fluid conduit and configured to connect to a fluid source providing the second fluid; and
- a second valve disposed in one of the connector or the fluid conduit and configured to: (i) allow the second fluid to flow in a first direction toward the at least one of the channel and the reservoir, and (ii) prevent the second fluid from flowing in a second direction opposite to the first direction such that a negative gauge pressure within the reservoir remains less than a predefined value.

19. The apparatus of claim 18, wherein the first fluid is atmospheric air, and the second fluid is an iontophoresis fluid including a therapeutic substance.

20. The apparatus of claim 18, wherein the first valve is an umbrella valve.

21. The apparatus of claim 18, wherein the predefined value is 1 kPa.

22. A method, comprising:
- inserting an apparatus into an ear canal of an ear such that a sealing element of the apparatus forms a seal against a surface of the ear canal to define a closed volume between a tympanic membrane of the ear and the apparatus, the apparatus including a body defining a channel and a reservoir, the channel and the reservoir in fluid communication with the closed volume after the apparatus has been inserted into the ear canal;
- delivering, via a fluid conduit of the apparatus, a first fluid into at least one of the closed volume, the channel, and the reservoir;
- venting, via a valve disposed through a wall of the reservoir, a second fluid from the reservoir; and
- preventing, via the valve, the second fluid from entering the reservoir through the valve when a differential pressure between an interior of the reservoir and an exterior of the apparatus is less than a predefined value.

23. The method of claim 22, further comprising providing the second fluid through the valve into the reservoir when the differential pressure is greater than the predefined value such that the differential pressure decreases.

24. The method of claim 22, wherein the predefined value is 1 kPa.

25. The method of claim 22, wherein the first fluid is an iontophoresis fluid including a therapeutic substance, and the second fluid is atmospheric air.

26. The method of claim 22, wherein the venting includes venting the second fluid from the reservoir such that a pressure within the ear canal does not increase.

* * * * *